United States Patent
Laufer et al.

(10) Patent No.: US 9,452,975 B2
(45) Date of Patent: Sep. 27, 2016

(54) BIOBASED CARBODIIMIDES, A PROCESS FOR PREPARATION THEREOF AND USE THEREOF

(71) Applicant: RHEIN CHEMIE RHEINAU GmbH, Mannheim (DE)

(72) Inventors: Wilhelm Laufer, Ellerstadt (DE); Armin Eckert, Oberhausen (DE); Franco Orsini, Ilbesheim (DE); Robert Eiben, Lampertheim (DE)

(73) Assignee: Rhein Chemie Rheinau GmbH, Mannheim (DE)

( * ) Notice: Subject to any disclaimer, the term of this patent is extended or adjusted under 35 U.S.C. 154(b) by 0 days.

(21) Appl. No.: 14/284,863

(22) Filed: May 22, 2014

(65) Prior Publication Data

US 2014/0323754 A1 Oct. 30, 2014

Related U.S. Application Data

(62) Division of application No. 13/698,755, filed as application No. PCT/EP2011/058219 on May 19, 2011, now abandoned.

(30) Foreign Application Priority Data

May 21, 2010 (EP) .................................... 10163621

(51) Int. Cl.
| | | |
|---|---|---|
| *C07C 267/00* | (2006.01) | |
| *C08G 18/28* | (2006.01) | |
| *C08G 18/36* | (2006.01) | |
| *C08G 18/42* | (2006.01) | |
| *C08G 18/79* | (2006.01) | |
| *C08K 5/29* | (2006.01) | |

(52) U.S. Cl.
CPC .......... *C07C 267/00* (2013.01); *C08G 18/283* (2013.01); *C08G 18/36* (2013.01); *C08G 18/4288* (2013.01); *C08G 18/797* (2013.01); *C08K 5/29* (2013.01)

(58) Field of Classification Search
None
See application file for complete search history.

(56) References Cited

U.S. PATENT DOCUMENTS

| | | | |
|---|---|---|---|
| 2,941,956 A | 6/1960 | Bergstrom | |
| 5,210,170 A * | 5/1993 | Quiring et al. | ................. 528/80 |
| 6,498,225 B2 | 12/2002 | Tebbe et al. | |
| 7,125,950 B2 * | 10/2006 | Dwan'Isa et al. | ........... 528/74.5 |
| 7,273,902 B2 | 9/2007 | Takahashi et al. | |
| 7,566,406 B2 | 7/2009 | Gilder | |
| 7,989,647 B2 | 8/2011 | Geiger et al. | |
| 2003/0088030 A1 * | 5/2003 | Haberle et al. | ............ 525/326.6 |
| 2006/0251881 A1 * | 11/2006 | Gilder | ........................ 428/317.1 |
| 2011/0155960 A1 * | 6/2011 | McAfee | ........................ 252/403 |

FOREIGN PATENT DOCUMENTS

| | | |
|---|---|---|
| DE | 1130594 B | 5/1962 |
| FR | 1180370 A | 6/1959 |

OTHER PUBLICATIONS

International Search Report from International Application PCT/EP2011/058219 dated Aug. 2, 2011, 3 pages.

\* cited by examiner

*Primary Examiner* — Karl J Puttlitz

(57) ABSTRACT

The present invention relates to novel biobased carbodiimides, a process for production thereof and use thereof. The biobased carbodiimides according to the invention comprise the reaction product of at least one carbodiimide and a carbon acid compound isolated or produced from renewable raw materials and having a functionality>1 and/or a hydroxy carboxylic ester having 2-24 carbon atoms.

8 Claims, 2 Drawing Sheets

BIOBASED CARBODIIMIDES, A PROCESS FOR PREPARATION THEREOF AND USE THEREOF

This application is a divisional of U.S. patent application Ser. No. 13/698,755 filed Jul. 3, 2013, entitled "Biobased Carbodiimides, a Process for Preparation Thereof and Use Thereof", which claims the right of priority under 35 U.S.C. §119 (a)-(d) and 35 U.S.C. §365 of International Application No. PCT/EP2011/058219, filed May 19, 2011, which is entitled to the right of priority of European Patent Application No. 10163621.5 filed May 21, 2010, the contents of which are hereby incorporated by reference in their entirety.

The present invention relates to novel biobased carbodiimides, a process for production thereof and use thereof. The biobased carbodiimides according to the invention comprise the reaction product of at least one carbodiimide and at least one carbon acid compound isolated or produced from renewable raw materials and having a functionality>1 and/or a hydroxy carboxylic ester having 2-24 carbon atoms.

Organic carbodiimides are known and are used, for example, as a stabilizer against the hydrolytic degradation of compounds containing ester groups. They are used mainly, for example, in the field of polyaddition and poly-condensation products, particularly polyurethanes and thermoplastic polyesters.

Polymers are increasingly required to be based on natural raw materials, for example biobased polyols (natural oil polyols, biopolyols). For instance, the U.S. Government launched a new programme in 2002 whereby such products may be declared "green" if they include more than 7% of a biobased raw material in the herein contemplated use sector of polyurethanes for house insulation.

Regrettably, biopolyols cannot simply replace petropolyols since they can have disadvantages relating to viscosity, defined functionality (OH groups per molecule), ageing behaviour, odour and other factors.

These "green products" have in the meantime also come to be used in the production of polyurethanes and foams, see U.S. Pat. No. 7,125,950, U.S. Pat. No. 7,566,406.

There is accordingly a need to make these "green products" also usable in the hydrolysis stabilizer sector.

The problem addressed by the present invention was therefore that of providing novel carbodiimides which are classifiable as "a green product" and have equivalent properties to prior art carbodiimides.

The problem addressed by this invention was solved by the novel modified carbodiimides, which are biobased.

The present invention accordingly provides biobased carbodiimides obtainable from the reaction of at least one carbodiimide and at least one carbon acid compound isolated or produced from renewable raw materials and having a functionality>1 and more than 4 carbon atoms and/or a hydroxy carboxylic ester.

Suitable carbodiimides for the purposes of the present invention are, in particular, monomeric or polymeric carbodiimides.

Carbodiimides for the purposes of the invention are preferably compounds of the general formula

$$R'-(-N=C=N-R-)_m-R''$$ (I), where

R represents an aromatic, aliphatic, cycloaliphatic or araliphatic radical which in the case of an aromatic or araliphatic radical may bear aliphatic and/or cycloaliphatic substituents having at least two carbon atoms, preferably branched or cyclic aliphatic radicals having at least 3 carbon atoms, more particularly isopropyl groups, in at least one position ortho, preferably in both positions ortho, to the aromatic carbon atom bearing the carbodiimide group, R'=$C_1$-$C_{18}$-alkyl, $C_5$-$C_{18}$-cycloalkyl, aryl, $C_7$-$C_{18}$-aralkyl or R—NCO, R—NHCONHR$^1$, R—NHCONR$^1$R$^2$ or R—NHCOOR$^3$, and R" denotes —NCO, where, in R', R$^1$ and R$^2$ are each independently the same or different and signify a $C_1$-$C_6$-alkyl, $C_6$-$C_{10}$-cycloalkyl or $C_7$-$C_{18}$-aralkyl radical and R$^3$ has one of the meanings of R$^1$ or denotes a polyester or polyamide radical, for example acetate or butyl and/or benzoic ester, and m is an integer from 1 to 5000 and preferably from 1 to 500.

Aromatic R is preferably aryl. Araliphatic R is preferably $C_7$-$C_{18}$-aralkyl, to which the "N=C=N" group can be attached not only via the alkyl radical but also via the aryl radical, aliphatic R is preferably linear or branched, optionally substituted $C_1$-$C_{18}$alkyl, and cycloaliphatic R is preferably optionally substituted $C_5$-$C_{19}$ cyclo or bicycloalkyl. Particularly suitable carbodiimides have the general formula (II) where the ortho positions relative to the carbodiimide group are substituted by isopropyl and the para position relative to the carbodiimide group is likewise substituted by isopropyl, for example

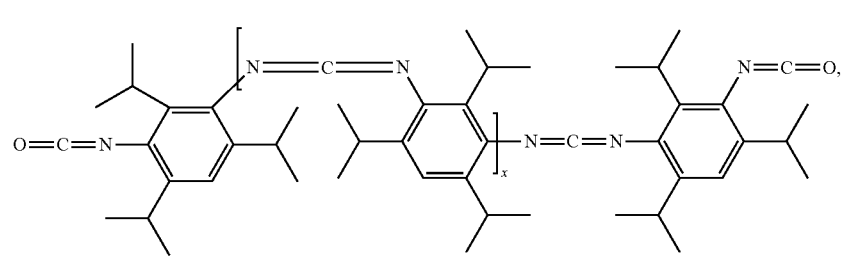

(II)

where x=1 to 50, preferably 2-20.

In a further preferred embodiment of the invention, the carbodiimide comprises a compound of formula (III)

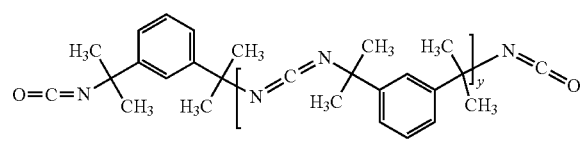

(III)

where y=1 to 20, preferably 2-8.

It is further also possible to use polymeric aliphatic carbodiimides, for example on the basis of isophorone diisocyanate or dicyclohexylmethane 4,4'-diisocyanate (H12-MDI=hydrogenated MDI).

The aforementioned carbodiimides comprise commercially available compounds which are commercially available for example from Rhein Chemie Rheinau GmbH under the trade names Stabaxol® P100 (N—C—N content: 13-14%), Stabaxol® P400, (N—C—N content: 13-14%) and Stabaxol® P 220 (N—C—N content: 13-14%). The products available from Raschig as Stabilisator 9000 and 11000 can also be used for the purposes of the present invention.

It is similarly also possible to prepare the carbodiimides by the processes described in U.S. Pat. No. 2,941,956 for example, or by the condensation of diisocyanates with elimination of carbon dioxide at elevated temperatures, for example at 40° C. to 200° C., in the presence of catalysts. Suitable processes are described in DE-A-11 30 594 and in FR 1 180 370. Examples of useful catalysts are strong bases or phosphorus compounds. Preference is given to using phospholene oxides, phospholidines or phospholine oxides, and also the corresponding sulphides. It is further possible to use tertiary amines, basic metal compounds, carboxylic acid metal salts and non-basic organometal compounds as catalysts.

Any isocyanate is useful for producing the carbodiimides and/or polycarbodiimides used, although the carbodiimides and/or polycarbodiimides preferably used in the context of the present invention are based on aromatic isocyonates substituted by $C_1$ to $C_4$-alkyl, for example 2,6-diisopropylphenyl isocyanate, 2,4,6-triisopropylphenyl 1,3-diisocyanate, 2,4,6-triethylphenyl 1,3-diisocyanate, 2,4,6-trimethylphenyl 1,3-diisocyanate, 2,4'-diisocyanatodiphenylmethane, 3,3',5,5'-tetraisopropyl-4,4'-diisocyanatodiphenylmethane, 3,3',5,5'-tetraethyl-4,4'-diisocyanatodiphenylmethane, tetramethylxylene diisocyanate, 1,5-naphthalene diisocyanate, 4,4'-diphenylmethane diisocyanate, 4,4'-diphenyldimethylmethane diisocyanate, 1,3-phenylene diisocyanate, 1,4-phenylene diisocyanate, 2,4-tolylene diisocyanate, 2,6-tolylene diisocyanate, a mixture of 2,4-tolylene diisocyanate and 2,6-tolylene diisocyanate, hexamethylene diisocyanate, cyclohexane 1,4-diisocyanate, xylylene diisocyanate, isophorone diisocyanate, dicyclohexylmethane 4,4'-diisocyanate, methylcyclohexane diisocyanate, tetramethylxylylene diisocyanate, 2,6-diisopropylphenylene isocyanate and 1,3, 5-triisopropylbenzene 2,4-diisocyanate or mixtures thereof, or based on substituted aralkyls, such as 1,3-bis(1-methyl-1-isocyanatoethyl)benzene. It is particularly preferable for the carbodiimides and/or polycarbodiimides to be based on 2,4,6-triisopropylphenyl 1,3-diisocyanate.

Polycarbodiimides, when obtained from isocyanates, may additionally contain still reactive NCO groups and complex-bound monomeric isocyanates.

In a further embodiment of the present invention, a mixture of various carbodiimides may be used. When a mixture of carbodiimides is used, the carbodiimides used may be selected from the group of monomeric and/or polymeric carbodiimides, in which case the above observations concerning the compounds of the general formulae (I) to (III) are referenced.

The term functionality for the purposes of the invention only comprehends the reactive compounds capable of reacting with isocyanates to form substituted urethane and/or urea derivatives.

Hydroxy carboxylic esters for the purposes of the present invention preferably comprise hydroxyl carboxylic esters of 2-24 carbon atoms, such as oligolactic acid for example, and/or polyhydroxybutyrates of formula (IV)

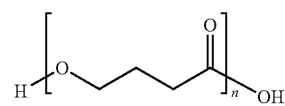

where n=2-20.

The carbon acid compounds isolated from renewable raw materials and having a functionality>1 preferably comprise natural polyols (biopolyols), for example castor oil, tall oil, starch and/or sugar.

The aforementioned compounds are commercially available.

Biopolyols typically have the characteristic triglyceride structure of a plant oil. Unlike petrochemically produced polyols (petropolyols) they do not have long ethylene oxide (EO) or propylene oxide (PO) chains. Biopolymers are also not as homogeneous as petropolyols, they usually also still contain double bonds, for example castor oil (shown in idealized form hereinbelow).

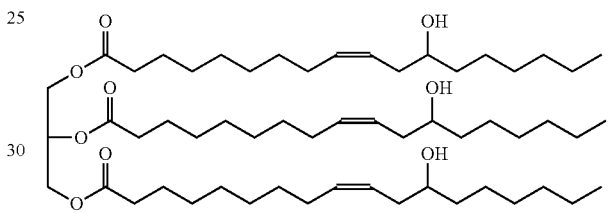

The carbon acid compounds produced from renewable raw materials and having a functionality>1 are preferably polyols from plant oils, for example rapeseed oil or soy oil, hereinbelow shown in idealized form:

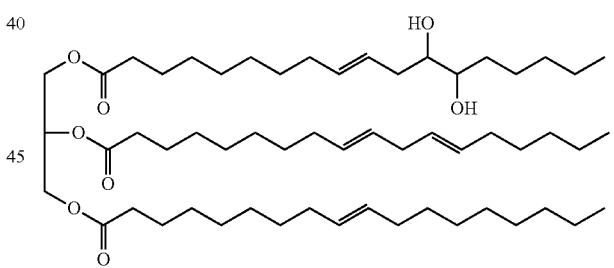

and/or from unsaturated fatty acids, for example oleic acid.

The aforementioned compound is commercially available, for example from Cargill and/or Urethane Soy Systems.

Conversion from plant oils or from unsaturated fatty acids can take place according to methods familiar to a person skilled in the art, for example ozonization with subsequent glycolysis, epoxidation with subsequent ring opening by, for example, alcohols or hydroformylation and subsequent reduction with hydrogen.

In a further embodiment of the present invention, the carbon acid compounds isolated or produced from renewable raw materials and having a functionality>1 and/or the hydroxy carboxylic esters are used in admixture with common non-biobased polyols based on polyether, polyester and/or polyetherester, obtainable from Bayer AG, BASF AG, etc.

The proportion of biobased raw materials should preferably not be below 7%, based on the biobased carbodiimide.

The biobased carbodiimides according to the invention are preferably obtainable via the reaction of at least one carbodiimide with at least one carbon acid compound isolated or produced from renewable raw materials and having a functionality>1 and/or the hydroxy carboxylic ester at temperatures between 20 and 200° C. and preferably 80-90° C., in solution and/or in the absence of a solvent in the presence or absence of at least one catalyst.

The present invention also provides a process for producing the carbodiimides of the invention, wherein at least one carbodiimide is reacted with at least one carbon acid compound isolated or produced from renewable raw materials and having a functionality>1 and/or the hydroxy carboxylic ester and optionally non-biobased polyols based on polyether, polyester and/or polyetherester at temperatures between 20 and 200° C., preferably 80-90° C., in solution and/or in the absence of a solvent in the presence or absence of a catalyst.

The reaction in solution is preferably carried out using toluene, xylene, ethyl acetate, butyl acetate and/or methyl ethyl ketone as solvent, with temperatures of 80-120° C. being preferred for the reaction, depending on the solvent.

Any catalyst known for this reaction can be used. Preference is given to tertiary amines, matrix-soluble tin compounds, such as dibutyltin dilaurate for example, titanium compounds, such as alkali metal titanates for example, and/or alternatively lead, bismuth and/or zinc compounds.

The modified (biobased) carbodiimides thus obtained satisfy the criterion of a "green" product.

The ratio of the carbodiimide to the carbon acid compound or the hydroxy carboxylic ester is preferably in the range from 5:95 to 95:5, more preferably in the range from 7:93 to 60:40 and even more preferably in the range from 7:93 to 50:50.

The reaction of the carbon acid compound or the hydroxy carboxylic ester with the carbodiimide is preferably carried out at temperatures of 20° C. to 200° C., more preferably 25° C. to 150° C. and even more preferably 80° C. to 120° C., while the mixing time can be 0.1 min to 360 min, preferably 1 min to 180 min and more preferably 5 min to 120 min.

The carbodiimides according to the invention are very useful as an acceptor for free carboxylic acids and therefore are preferably used as stabilizers against the hydrolytic degradation of compounds containing ester groups, for example polymers containing ester groups, e.g. polycondensation products, such as for example thermoplastic polyesters, such as polyethylene terephthalate, polybutylene terephthalate, polyetheresters, polyamides, polyesteramides, polycaprolactones and also unsaturated polyester resins and polyesteresters, e.g. block copolymers of polyethylene terephthalate or polybutylene terephthalate and polycaprolactone, and polyaddition products, e.g. polyurethanes, polyureas and polyurethane-polyurea elastomers containing ester groups.

These compounds containing ester groups are generally known. Their starting materials, methods of preparation, structures and properties are extensively described in the standard literature. Owing to their ready solubility in the components for synthesizing polyurethanes and their high compatibility with the polyurethanes formed, the (poly) carbodiimides according to the invention are particularly useful as stabilizers against the hydrolytic degradation of polyurethanes, preferably compact or cellular polyurethane elastomers and more particularly thermoplastic polyurethanes and also cellular or compact elastomers.

The present invention accordingly also provides for the use of the carbodiimides according to the invention in polyurethane applications, for rigid foam/coatings, flexible foam, CASE (Coatings, Adhesives, Sealants, Elastomers), thermoplastics, for hydrolysis control, in lubricant applications, such as ester-based oils for example, in transformer oils and for crosslinking of polyurethanes.

The examples which follow serve to illustrate the invention in a non-limiting manner.

EXEMPLARY EMBODIMENTS

Example 1

Preparation of Biobased Carbodiimide A
(According to the Invention)

101.0 g of Stabaxol® P220, a polymeric carbodiimide based on tetramethylxylyene diisocyanate (NCN content about 14%), were charged, and heated to 100° C., under nitrogen.

To this were added 41.0 g of polyethylene glycol (monomethyl ether) having an OH number of 165.7 and 38.5 g of Soyol® R2-052-C (biobased polyester polyol from Urethane Soy Systems=biopolyol) having an OH number of 65.2. This was followed by stirring for a further 330 min, standing overnight and heating the next day to 120° C. and a further 240 min of stirring at 120° C. The biopolyol proportion is 21%.

Acid degradation with this biobased carbodiimide A

As will be known, the efficacy of a hydrolysis control agent based on sterically hindered carbodiimides can be tested in liquid polyester polyols via acid degradation.

The efficacy of the biobased carbodiimide was tested in the biobased polyester polyol (Soyol® R2-052-C from Urethane Soy Systems=biopolyol).

At 100° C., 2% or 4% of the abovementioned biobased carbodiimide A (samples (A)) was stirred into the biopolyol and the acid number was measured at regular intervals. The results are shown in FIG. 1.

Acid degradation is clearly visible in both cases. The efficacy of the biobased carbodiimide is hence comparable to that of the non-biobased carbodiimide Stabaxol® P 200 (samples (C)), see FIG. 1, which also contains, for comparison, 1 and 2% of (C) (Stabaxol® P 200).

Example 2

Production of Biobased Carbodiimide B (According to the Invention)

200 g of Stabaxol® P 220, a polymeric carbodiimide based on tetramethylxylylene diisocyanate (NCN content about 14%), was initially charged, and heated to 140° C., under nitrogen.

To this were added 238 g of Agrol 2.0, a biobased polyol from Cargill of OH number 74.5.

The mixture was then stirred until the NCO content had dropped to zero. The proportion of biopolyol was 54%.

Acid Degradation with this Biobased Carbodiimide B

The efficacy of the biobased carbodiimide B was tested in the biobased polyester polyol (Soyol® T 22-60-C from Urethane Soy Systems=biopolyol).

At 100° C., 1% or 2% of the abovementioned biobased carbodiimide B (samples (B)) was stirred into the biopolyol and the acid number was measured at regular intervals. The results are shown in FIG. 2. In both cases, acid degradation is clearly visible.

The efficacy of the biobased carbodiimide is hence comparable to that of the non-biobased carbodiimide Stabaxol® P 200 (samples (C)), see FIG. 2, which also contains, for comparison, 1 and 2% of (C) (Stabaxol® P 200).

Figure 1:
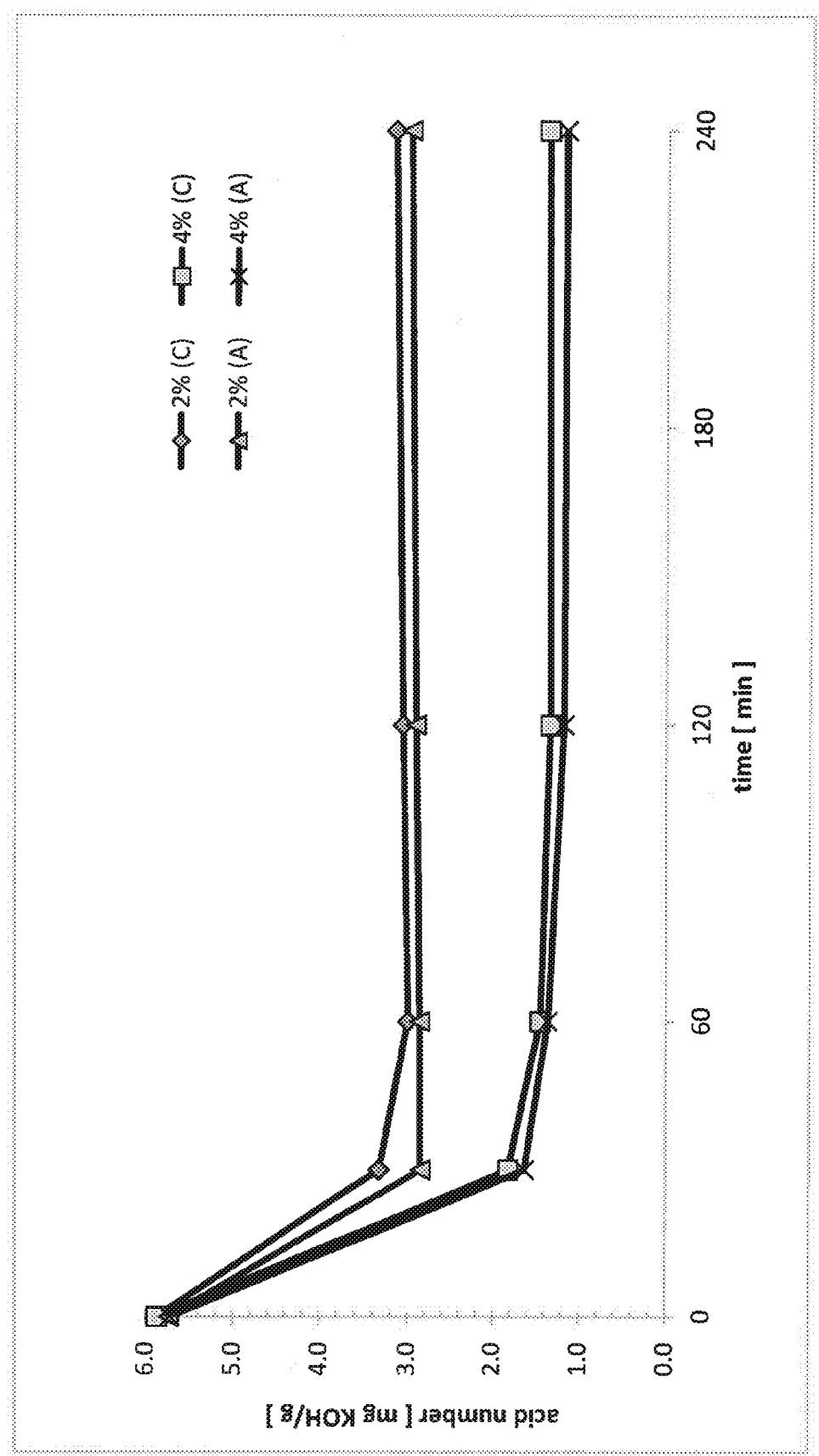
FIG. 1 schematically illustrates the results of an acid number measurement of example 1.
Figure 2:
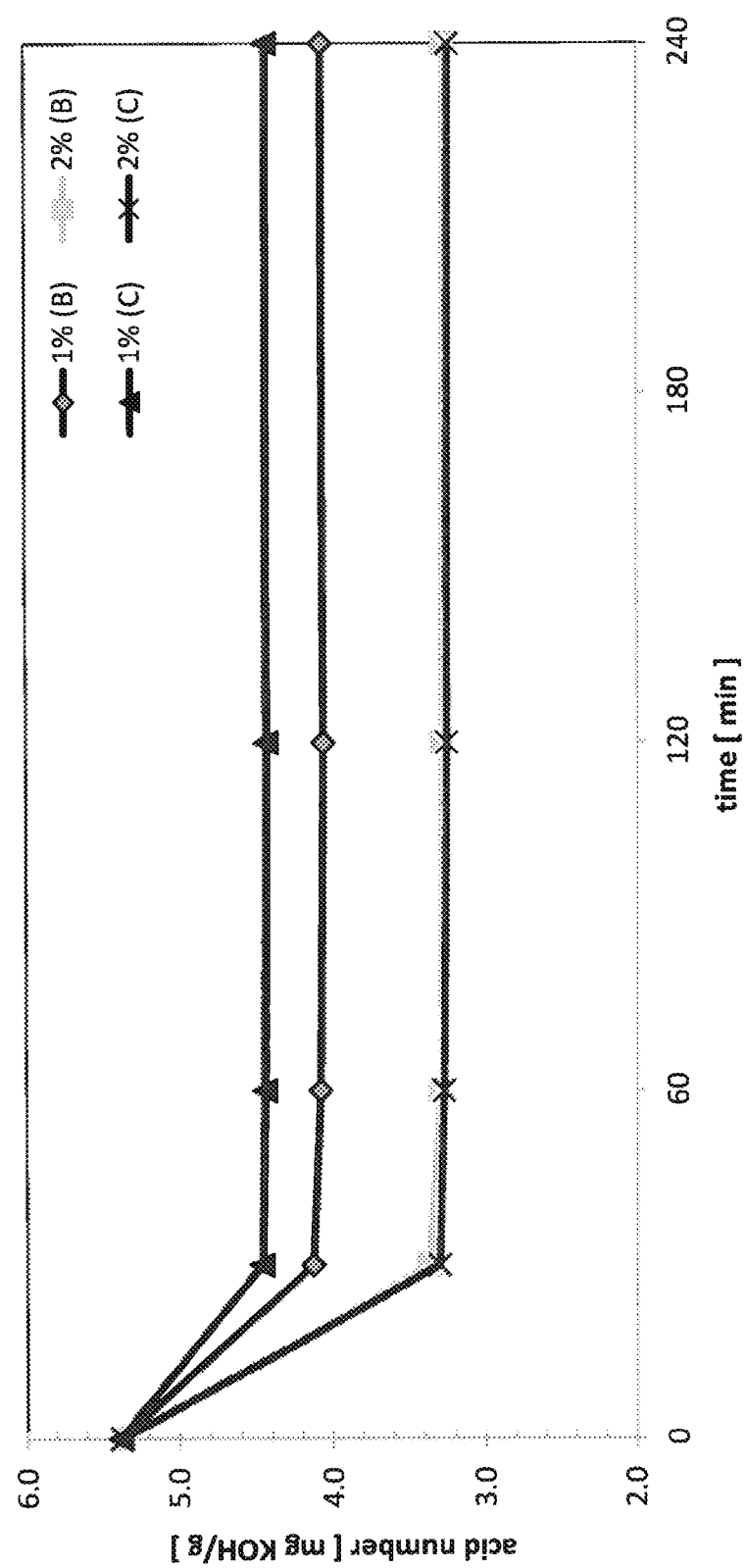
FIG. 2 schematically illustrates the results of an acid number measurement of example 2.

What is claimed is:

1. A process for stabilizing a compound containing ester groups, against hydrolytic degradation, the process comprising:
    contacting a compound containing ester groups with a biobased carbodiimide produces by reacting at least one carbodiimide and at least one carbon acid compound at a temperature of 20° C. to 200° C.,
    wherein the carbodiimide comprises:
        a compound of formulae (II),

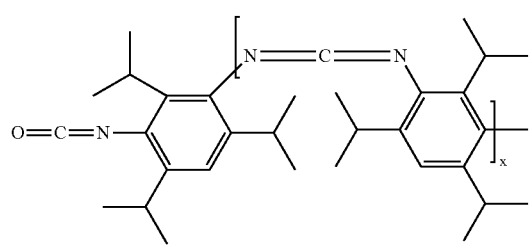

(II)

where x =1 to 50 ;
a compound of formulae (III),

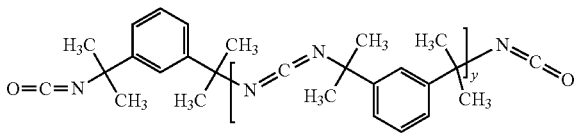

(III)

where y=1 to 20, and /or
    dicyclohexylmethane 4,4'-diisocyanate (H 12-MDI=hydrogerated MDI); and
wherein the at least one carbon acid compound has a functionality greater than 1, comprises greater than 4 carbon atoms, and is from a renewable source selected from the group consisting of castor oil, rapeseed oil, soy oil, tall oil, and combinations thereof.

2. The process according to claim 1, wherein the ratio of the carbodiimide to the carbon acid compound is 5:95 to 95:5.

3. The process according to claim 1, wherein the biobased carbodiimide further comprises a non-biobased polyol based on polyether, polyester and/or polyetherester.

4. A process for stabilizing compounds containing ester groups from hydrolytic degradation with a biobased stabilizing agent, the process comprising:
    contacting the compounds containing ester groups with a biobased, green stabilizing agent produced by a process comprising:
        contacting at least one carbon acid compound having a functionality>1and more than 4 carbon atoms from renewable raw materials selected from a group that includes castor oil, rapeseed oil, soy oil, tall oil, and mixtures of these, with at least one carbodiimide selected from:
            dicyclohexylmethane 4,4'-diisocyanate,
            compounds of formulae (II)

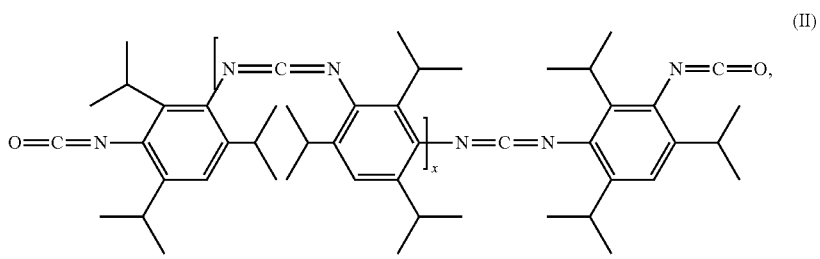

(II)

where x =1 to 50, and/or
compounds of formula (III)

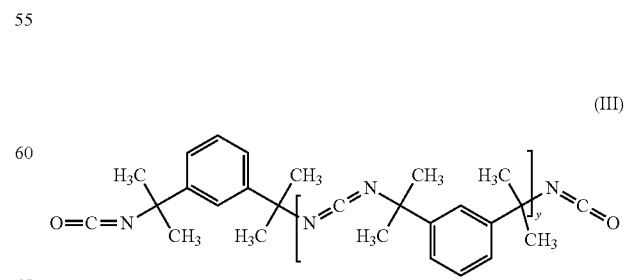

(III)

where y =1 to 20,

-continued

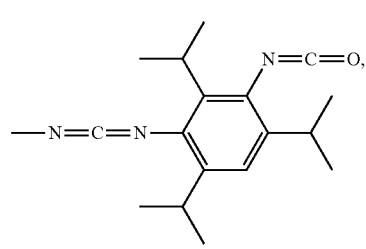

in solution and/or in the absence of a solvent in the presence or absence of a catalyst to produce the biobased carbodiimide stabilizing agent, to stabilize the compound containing ester groups against hydrolytic degradation.

5. The process according to claim 4, wherein the contacting is done at a temperature of 20° C. and 200° C. at a ratio of the carbodiimide to the carbon acid compound of 5:95 to 95:5.

6. The process according to claim 5, wherein the contacting of the at least one carbon acid compound with the at least one carbodiimide comprises reacting the at least one carbon acid compound with the at least one carbodiimide at temperatures of 80° C. to 120° C. in the presence of a solvent selected from the group consisting of toluene, xylene, ethyl acetate, butyl acetate and/or methyl ethyl ketone.

7. The process according to claim 5, wherein the contacting of the at least one carbon acid compound with the at least one carbodiimide comprises reacting the at least one carbon acid compound with the at least one carbodiimide in the presence of a catalyst selected from the group consisting of tertiary amines, matrix-soluble tin compounds, titanium compounds, lead, bismuth, and zinc compounds.

8. The process according to claim 4, wherein:
the ratio of the carbodiimide to the carbon add compound is 5:95 to 95:5;
the contacting of the at least one carbon add compound with the at least one carbodiimide comprises reacting the at least one carbon acid compound with the at least one carbodiimide at a temperature of 80° C. to 120' C.;
the reacting is done in the presence of a solvent selected from the group consisting of toluene, xylene, ethyl acetate, butyl acetate and/or methyl ethyl ketone; and
the reacting is done in the presence of a catalyst selected from the group consisting of tertiary amines, matrix-soluble tin compounds, titanium compounds, lead, bismuth, and zinc compounds.

* * * * *